(12) United States Patent
Leonard et al.

(10) Patent No.: US 8,258,184 B1
(45) Date of Patent: *Sep. 4, 2012

(54) USE OF VEGETABLE BUTTER-BASED CETYL MYRISTOLEATE FOR TREATING OSTEOARTHRITIS AND OTHER MUSCULOSKELETAL DISEASE CONDITIONS AND INJURIES

(75) Inventors: Edward C. Leonard, Memphis, TN (US); Dori Simonton, Broken Bow, NE (US)

(73) Assignee: Botanoceuticals, Inc., Englewood Cliff, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/823,241

(22) Filed: Jun. 25, 2010

Related U.S. Application Data

(63) Continuation of application No. 10/103,447, filed on Mar. 21, 2002, now Pat. No. 7,772,279.

(51) Int. Cl.
*A61K 31/22* (2006.01)

(52) U.S. Cl. ........................................... 514/549

(58) Field of Classification Search ............. None
See application file for complete search history.

(56) References Cited

U.S. PATENT DOCUMENTS

| | | | |
|---|---|---|---|
| 4,113,881 A | 9/1978 | Diehl |
| 5,569,676 A | 10/1996 | Diehl |
| 6,489,494 B1 | 12/2002 | Leonard |
| 6,677,321 B1 | 1/2004 | Levin |

OTHER PUBLICATIONS http://www.solidgoldnorthwest.com/response/joi_hum.html retrieved from the web on Jan. 11, 2011.*
The Merck Manual, 17th Edition, pp. 407-408, (1999).

* cited by examiner

*Primary Examiner* — Phyllis G. Spivack
(74) *Attorney, Agent, or Firm* — Wyatt, Tarrant & Combs, LLP; H. Roy Berkenstock

(57) ABSTRACT

A vegetable butter based dietary supplement of cetyl myristoleate for use in the treatment of osteoarthritis and other joint inflammatory diseases of the musculoskeletal system in animals, especially equines. In its preferred form, the cetyl myristoleate is a vegetable butter-based and is administered in doses of about 1750 to about 6750 mg. The dosage may also include 3000 mg methylsulfonylmethane, 3000 mg glucosamine HCL and 1000 mg of Vitamin C.

2 Claims, 1 Drawing Sheet

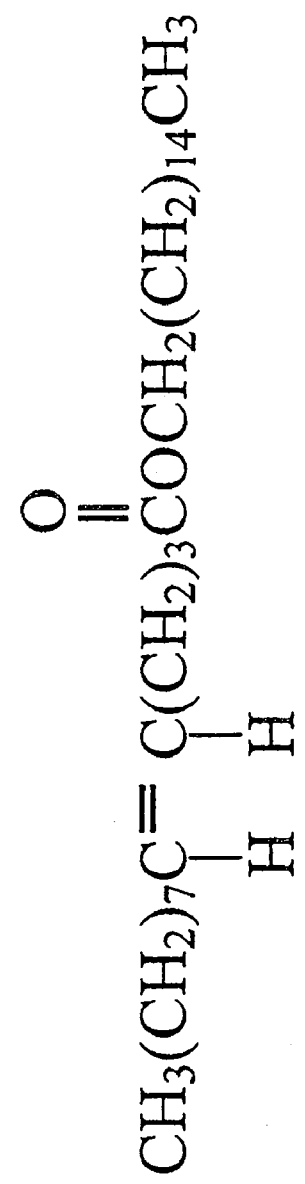

USE OF VEGETABLE BUTTER-BASED CETYL MYRISTOLEATE FOR TREATING OSTEOARTHRITIS AND OTHER MUSCULOSKELETAL DISEASE CONDITIONS AND INJURIES

CROSS REFERENCE TO RELATED APPLICATIONS

The present application is a Continuation of U.S. patent application Ser. No. 10/103,447, filed Mar. 21, 2002 now U.S. Pat. No. 7,772,279 and claims priority under 35 U.S.C. §120, and incorporates such application in its entirety.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to the dietary supplement, cetyl myristoleate. More particularly, the present invention relates to the use of cetyl myristoleate derived exclusively from vegetable sources as a treatment for osteoarthritis and other inflammatory diseases of the musculoskeletal system in animals, specifically equines. In addition, the present invention also relates to the treatment of injuries and stress-related trauma that adversely affect the orthopedic and muscular systems of horses.

2. General Background of the Invention

Nearly 50% of the Western world population over 65 has chronic, painful, disabling arthritis in one form or another of the disease. New prescription drugs, most notably Vioxx® and Celebrex® offered for arthritis relief have efficacy for large numbers of patients. Each of these drugs has achieved U.S. sales of billions of dollars in a relatively short time. Unfortunately, these chemically and biologically very powerful drugs have resulted in adverse reactions in a small minority of patients, some of which have been fatal.

There are a number of dietary supplements on the market that purport to offer relief for arthritis; glucosamine and chondroitin are examples. Dietary supplements need no prescription. Glucosamine has been on the market for two decades and has achieved annual U.S. sales of more than one hundred million dollars.

Research has shown that another dietary supplement, cetyl myristoleate, is a remedy for patients with osteoarthritis, rheumatoid arthritis, and other joint disorders. Cetyl myristoleate (CM), as an arthritis palliative, was discovered by Harry Diehl in 1964. Through his research, he showed that CM protected Swiss albino mice from arthritis as well as laboratory rats exposed to Freund's adjuvant. U.S. Pat. No. 5,569,676, U.S. Pat. No. 4,113,881, U.S. Pat. No. 4,049,824 were granted for the use of cetyl myristoleate for the prevention and treatment of various forms of arthritis.

Until 1999, all commercial cetyl myristoleate was based on a mixture of "bovine" straight-chain fatty acids containing mainly two 14-carbon, straight-chain fatty acids, myristic and myristoleic. The commercial source of these fatty acids was beef tallow, a by-product of the beef rendering industry. The beef tallow, which is a triglyceride (glycerol triester), is split to produce free fatty acids and glycerine. Large fatty acid commercial producers then fractionate the fatty acids by distillation, with the high myristoleic acid-containing stream one fraction out of many possibilities. Esterification of these fatty acids with cetyl alcohol forms cetyl myristoleate and cetyl myristoleate. Unfortunately, while tallow-based CM products can be used to treat arthritis in humans, tallow-based cetyl myristoleate is not palatable for horses. Horses are naturally herbivores, they do not eat meat. When the tallow-based CM product is mixed with their grain, the horses refuse to eat it. This makes the treatment of arthritis and other musculoskeletal conditions in horses with conventional tallow-based CM very difficult.

BRIEF SUMMARY OF THE INVENTION

The method of the present invention provides a treatment for orthopedic and musculoskeletal diseases in animals. Specifically, the method of the present invention solves the problem of treating osteoarthritis and other musculoskeletal conditions as well as injuries and stress-related trauma that adversely affect the orthopedic and muscular systems of equines, specifically horses, by using cetyl myristoleate isolated from a vegetable source.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawing, wherein:

FIG. 1 shows the chemical formula of cetyl myristoleate.

DETAILED DESCRIPTION OF THE INVENTION

The present invention provides a novel method of treating osteoarthritis and other musculoskeletal conditions in animals with a vegetable source of cetyl myristoleate (CM), and preferably a vegetable oil or butter-based source. The treatment of horses suffering from arthritis has proved difficult. Despite the successful treatment of humans with CM, horses have found the tallow-based CM unpalatable. Horses refuse to eat feed containing a tallow-based CM product. Even when this tallow-based CM product also contains molasses and apple flavorings, the tallow-based CM product is refused. Thus, they have been unable to take advantage of the benefits of CM-based therapies for a variety of musculoskeletal conditions.

CM is a compound derived from myristoleic acid. Until recently, myristoleic acid was only sourced from animal origins. However, in 1999, it was discovered unexpectedly, that myristoleic acid could be obtained from a vegetable butter source[1].

There is a tree that produces a nut containing a vegetable butter that is a relatively good source of myristoleic acid. The fat is known as kombo butter. It comes from the seeds of Pycnanthus Kombo (Myristicaceae family) found in West Central Africa. Other compounds isolated from P. Kombo (P. Angolensis) include 2'-hydroxy-4'-7-dimethoxy isoflavone and 2'-hydroxy formonometin. In addition, U.S. Pat. No. 5,674,000 describes the isolation and use of terpenoid quinones from the stems and leaves (not the seedfat) of P. kombo for use in treating diabetes.

The seedfat of P. kombo is reddish-brown and has a distinct aromatic odor. The kernel resembles nutmeg in appearance. The odor is quite unique and thus, it is possible that it is the pleasant odor of the source origin of CM that makes the vegetable butter-based CM palatable to horses. It is also possible that unpleasant flavor components found in the beef-tallow based CM makes that CM unpalatable for horses, particularly since horses are herbivores.

Flavor chemistry is the "art of the small". Key flavor components are sometimes present in very small amounts. The vegetable oil-based cetyl myristoleate is derived in a 4-step manufacturing sequence starting with kombo butter. The tallow-based cetyl myristoleate is derived in one manufacturing step (esterification) from a tallow fatty acids fraction. Tallow fatty acids have a distinct odor and taste. Kombo butter also has a distinct odor and taste that does not remotely resemble the characteristics of tallow fatty acids. Furthermore, the tallow-based CM contains 1%-2% C13, C15, and C17 fatty acids 10 that are not present in kombo fatty acids. These fatty acids could □ be adverse flavor components that cause the tallow-based CM to be unpalatable.

In contrast, kombo butter contains about 20%-30% kombic acid. Although kombic acid is eliminated in the subsequent manufacturing steps, some trace components could be carried into the finished cetyl myristoleate to add a distinctive flavor. There are also trace amounts of sterols in the vegetable butter-based cetyl myristoleate. Sterols can have a sweetish taste. Any and all of these and other trace compounds can affect the tastes of the tallow-based and vegetable butter-based CM. The present invention shows, however, that whatever the actual difference is between the two sources of CM, horses can distinguish between the two and only accept the vegetable sourced CM. Thus, although the CM itself is the chemical important for the actual treatment of arthritis and other inflammatory musculoskeletal diseases, the source of that CM is unexpectedly extremely important in the ability of the horses to ingest the CM.

The present invention encompasses vegetable butter-based CM products used to treat osteoarthritis and other inflammatory musculoskeletal conditions in equines. Furthermore, the present invention also encompasses the use of vegetable butter-based CM to treat injuries and other stress-related traumas that adversely affect the orthopedic and muscular systems of horses.

Specifically, the present invention product comprises from about 50 mg to about 15,000 mg cetyl myristoleate derived from a vegetable source. This invention product can also comprise from about 0 mg to about 50,000 mg each of methylsulfonylmethane (MSM), glucosamine, and vitamin C. The present invention products also encompass other ingredients, such as flavorings.

The present invention also comprises at least two specific vegetable butter-based CM compounds, CetylM™ and Joint Response™. CetylM™ is comprised of 4500 mg cetyl myristoleate derived exclusively from a vegetable butter source, 3000 mg glucosamine HCl, 3000 mg MSM, and 1000 mg Vitamin C. In addition, CetylM™ is also comprised of alfalfa leaf; lecithin, vitamin E, L-methionine, zinc sulfate, calcium monophosphate, copper sulfate, citrus bioflavonoids, and selenium, all at low levels. A palatable sweet apple and molasses flavor base brings the total weight for 2 scoops to 70 grams. A single dose is considered '2 scoops' or 70 grams.

Joint Response™ is comprised of 4000 mg cetyl myristoleate derived exclusively from a vegetable butter source, 3500 mg glucosamine HCl, 2400 mg MSM, and 1200 mg Vitamin C. Joint Response™ is also comprised of alfalfa leaf; ascorbic acid, lecithin, vitamin E, L-methionine, zinc sulfate, calcium monophosphate, copper sulfate, citrus bioflavonoids and selenium, all at low levels. Again, as with CetylM, a palatable sweet apple and molasses flavor base brings the total weight for 2 scoops to 70 grams.

A typical dose is 70 grams, or from about 4000 mg to 4500 mg of vegetable butter-based CM product. The recommended dosage for an average size horse (that is, a horse weighing from about 900 lbs to about 1100 ibs) is 3 scoops (or 1.5 doses) twice a day for 10 to 30 days. This is considered the 'treatment period'. The CM product is loaded into the body and the beneficial results of the CM are largely seen during this time period. Then, the horse is maintained on 2 scoops (1 dose) daily, thereafter. This maintenance dose is needed for the rest of the horse's life or the horse will eventually regress back to pre-treatment conditions.

There are several breeds of larger size horses with a variety of joint problems. For horses over 1200 lbs, an additional scoop or 105 g of the CM product is indicated. For smaller horses, the dose would be adjusted down accordingly.

EXAMPLE 1

Treatment of Osteoarthritis in a Horse with Vegetable Butter-Based CM

A 25-year-old Appaloosa that had been used as a schooling horse when she was younger, developed large, swollen knees, was very stiff on the front end, and tripped a lot. She was very lame. She had tried yucca, a desert plant conventionally used as an anti-inflammatory, but the results were not noticeable. However, when she was treated with Joint Response, the vegetable butter based CM product, all mobility came back and the swelling went down. She became well enough to campaign in dressage and won first and second place.

EXAMPLE 2

Treatment of an Injury Affecting the Orthopedic and Muscular System of a Horse with Vegetable Butter-Based CM A 2-year-old horse reared up and caught his leg in a gate. He ripped the gate completely off and cut the tendons, the bone, and shattered his pastern. X-ray analysis by a veterinarian indicated that he would never be rideable. After treatment with Joint Response™, the vegetable butter-based CM compound, the quality of life of this horse has greatly improved and he is again considered useful.

EXAMPLE 3

Treatment of Osteoarthritis Caused by Injuries Affecting the 10□Orthopedic and Muscular System of a Horse with Vegetable Butter-Based CM A 30-year-old mare that used to be a working ranch horse sustained serious injuries over the years that resulted in severe arthritis. Previous treatments included Butte, MSM, Glucosamine, Electrolytes, "C" and Yucca powder to alleviate some of the discomfort, but it was not working nearly well enough. Joint Response was tried as a last resort. After 2 days of treatment, the horse was found walking around her pen. Less than two weeks after treatment, a 13-year-old child was able to ride her galloping up and down a dirt road.

All measurements disclosed herein are at standard temperature and pressure, at sea level on Earth, unless indicated otherwise. All materials used or intended to be used in a patient are biocompatible, unless indicated otherwise.

REFERENCES

1. Banerji, R., Chowdhury, A. R., Misra, G., Nigam, S. K., Fette, Seifen, Anstrichmittel, "Butter From Plants", 86(7), p 283 (1984).

The foregoing embodiments are presented by way of example only; the scope of the present invention is to be limited only by the following claims.

What is claimed is:

1. A method of relieving symptoms of inflammatory diseases of the musculoskeletal system in equine mammals caused by osteoarthritis or an injury affecting the orthopedic or muscular system which comprises the oral administration of an effective amount of a vegetable-derived cetyl myristoleate administered with a compatible carrier in an amount of from about 1750 mg to about 6750 mg per dose which is administered twice a day for a treatment period from about 10 days to about 30 days.

2. The method of claim 1 wherein said effective amount of cetyl myristoleate is administered for the treatment period for from about 10 days to about 30 days and then a maintenance treatment of a single dose of the effective amount is thereafter administered once a day indefinitely.

* * * * *